United States Patent
Kameyama

(10) Patent No.: US 6,417,351 B1
(45) Date of Patent: *Jul. 9, 2002

(54) PROCESS FOR PRODUCING 3-ALKENYLCEPHEM COMPOUNDS

(75) Inventor: Yutaka Kameyama, Tokushima (JP)

(73) Assignee: Otsuka Kagaku Kabushiki Kaisha, Osaka-fu (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/424,260

(22) PCT Filed: Apr. 6, 1998

(86) PCT No.: PCT/JP98/02463

§ 371 (c)(1),
(2), (4) Date: Dec. 1, 1999

(87) PCT Pub. No.: WO98/55485

PCT Pub. Date: Dec. 10, 1998

(30) Foreign Application Priority Data

Jun. 4, 1997 (JP) .............................. 9-163403

(51) Int. Cl.[7] ...................... C07D 501/22; C07D 501/24
(52) U.S. Cl. ...................................... 540/215; 540/222
(58) Field of Search ................................ 514/215, 222

(56) References Cited

U.S. PATENT DOCUMENTS

| | | | | |
|---|---|---|---|---|
| 3,755,341 A | * | 8/1973 | Mendelson ............. | 260/297 R |
| 4,487,927 A | | 12/1984 | Takaya et al. ................. | 544/22 |
| 4,705,851 A | | 11/1987 | Takaya et al. ............... | 540/215 |
| 5,132,419 A | | 7/1992 | Lanz et al. .................. | 540/215 |
| 5,304,641 A | | 4/1994 | Cabri et al. ................. | 540/215 |
| 5,502,214 A | * | 3/1996 | Teicher ......................... | 548/950 |
| 5,541,175 A | * | 7/1996 | Yeo ............................. | 540/222 |
| 5,874,616 A | * | 2/1999 | Howells ...................... | 564/82 |
| 6,288,223 B1 | * | 9/2001 | Okada et al. ............... | 540/220 |

FOREIGN PATENT DOCUMENTS

| | | |
|---|---|---|
| JP | 61-269330 | 11/1986 |
| JP | 63-20435 | 4/1988 |
| JP | 3-120288 | 5/1991 |
| JP | 6-9646 | 1/1994 |

OTHER PUBLICATIONS

Katsura, Tet. Letters 35(51), Dec. 1994.*

* cited by examiner

*Primary Examiner*—Mark L Berch

(57) ABSTRACT

A process for preparing 3-alkenylcephem compounds characterized in that 3-alkenylcephem compound of the formula (3) is prepared in a single step by simultaneously conducting reactions of a 3-chloromethylcephem compound of the formula (1) with iodization reagent, alkali metal hydroxide or carbonate, arylphosphine and an aldehyde of the formula (2)

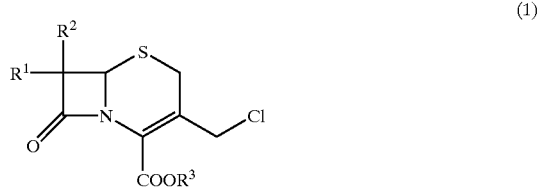

(1)

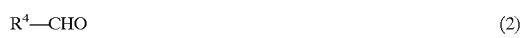

(2)

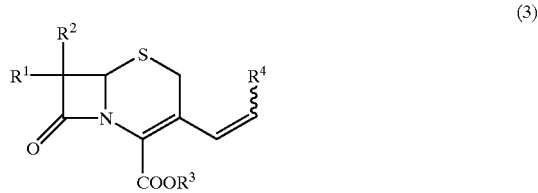

(3)

wherein $R^1$, $R^2$, $R^3$ and $R^4$ are as defined in the specification.

4 Claims, No Drawings

PROCESS FOR PRODUCING 3-ALKENYLCEPHEM COMPOUNDS

TECHNICAL FIELD

The present invention relates to a technique with which a stable 3-alkenylcephem compound is prepared in a single step in which an unstable intermediate generated in the reaction system is reacted with a reagent at the same time. The resulting 3-alkenylcephem compound is useful as an intermediate of Cefixime that is a useful antibacterial agent having a wide range antibacterial spectrum disclosed in, for example, Handbook of Latest Antibiotics, 9th ed., Katsuji Sakai P. 83 (JP-B-20435/1988).

BACKGROUND ART

As a process for preparing 3-alkenylcephem compounds, it is generally employed, when taking 3-vinylcephem compounds as example, to conduct Wittig reaction with form- aldehyde by using 3-chloromethylcephem derivative or 3-hydroxymethylcephem derivative as a starting material, as described in JP-B-20435/1988 and JP-A-263990/1986. In these processes, it is generally and widely employed that the reactions until phosphonium salt is obtained are conducted in one-pot and, after isolation of the phosphonium salt, ylidation is performed and the reaction with formaldehyde is resumed. In such a series of Wittig reaction, the respective compounds of iodide compound, phosphonium salt and ylide, each being intermediate, are often unstable, and thus it might be impossible to obtain a satisfactory yield. As a matter of fact, the reactions in JP-B-20435/1988 and JP-A-263990/1986 cause the problems that because of a temporal isolation of phosphonium salt, process is complicated and the total yield is low (the total yield of the former is 65%, and that of the latter is 52%). Further, both have many problems in practical production. For example, due to a low yield, by-products are formed in decomposition of the above-mentioned compounds. Accordingly, there has been a desire for an excellent reaction that is a short reaction step applicable industrially, and achieves a short residence time of unstable intermediates.

Process of JP-A-263990/1986:

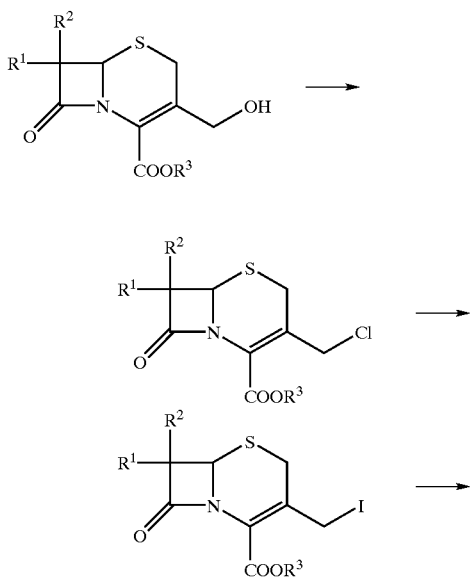

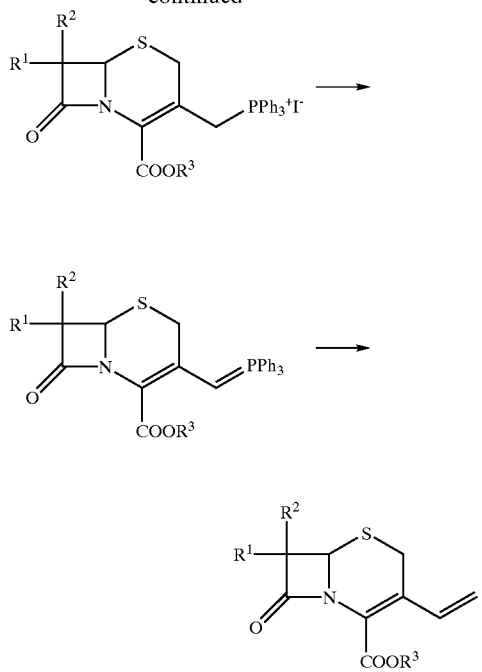

Alternatively, 3-vinylcephem compounds can be prepared by the reaction of allenyl β-lactam compound with copper chloride/vinyltributyl tin or vinylcuprate, as described in Tetrahedron Lett., 1992, 33, 7029, and J. Org. Chem., 1994, 59, 4956. In either case, a large amount of copper salt is required, and a significant number of problems may arise with its industrial application from an environmental point of view. Further, since allenyl β-lactam compound used in these reactions is unstable, there are also handling problems in a large scale reaction.

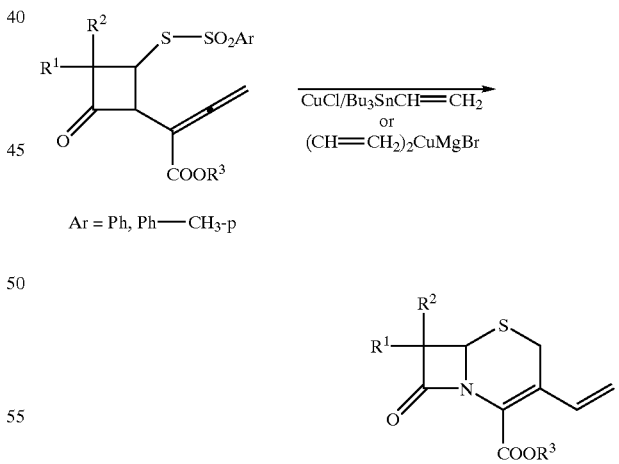

In the meanwhile, there has been reported a process of preparing 3-vinylcephem compounds by subjecting a 3-trifluoromethane sulfonyloxycephem compound or 3-fluorosulfonyloxycephem compound to coupling reaction or reaction with vinyl cuprate, by using an organic tin compound/palladium catalyst. (Tetrahedron Lett., 1988, 29, Tetrahedron Lett., 1990, 31, 3389, 6043, Tetrahedron Lett., 1991, 32, 4073, and Journal of Organic Chemistry, 1990, 55, 5833).

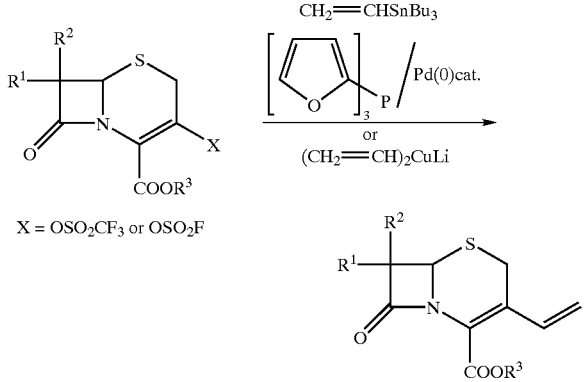

X = OSO₂CF₃ or OSO₂F

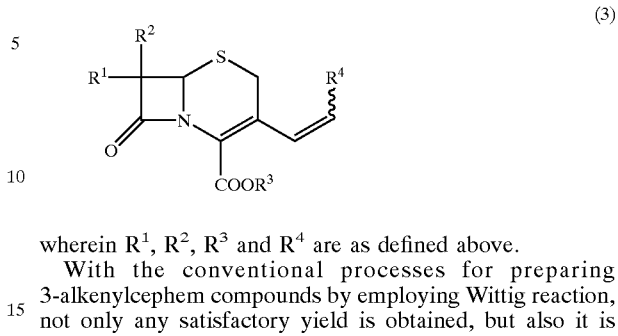

It is however difficult to industrially apply these processes because, when synthesizing a starting material, 3-trifluoromethanesulfonyloxycephem compound or fluoromethanesulfonyloxycephem compound is required to be prepared by using trifluoromethane sulfonic acid anhydride or fluorosulfonic acid anhydride, the industrial handling of which is difficult. It is also necessary to use an expensive palladium catalyst and copper reagent of not less than equivalent, in these reactions. Thus, there are a number of problems when these processes are put into practice.

Although the foregoing conventional techniques have been applied to not only a process for preparing 3-vinylcephem compounds but also 3-alkenylcephem compounds, there are essential problems remaining unsolved.

An object of the present invention is to provide a novel technique with which 3-alkenylcephem compounds can be prepared in a single easy handling with high yield, by using a 3-chloromethylcephem compound as a starting material, and simultaneously conducting reactions of iodization reagent, alkali metal hydroxide or carbonate, arylphosphine and aldehyde, to decrease the residence time of unstable intermediates in the system.

DISCLOSURE OF THE INVENTION

The present invention provides a process for preparing 3-alkenylcephem compounds characterized in that 3-alkenylcephem compound of the formula (3) is prepared in a single step by simultaneously conducting reactions of a 3-chloromethylcephem compound of the formula (1) with iodization reagent, alkali metal hydroxide or carbonate, arylphosphine and an aldehyde of the formula (2)

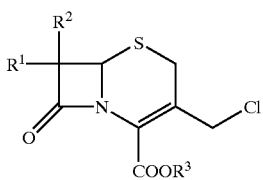

(1)

wherein $R^1$ is a hydrogen atom, halogen atom, amino group, protected amino group, or Ar—CH=N— group where Ar is aryl group which may have a substituent; $R^2$ is a hydrogen atom, halogen atom, lower alkoxy group, lower acyl group, lower alkyl group, lower alkyl group which has hydroxyl or protected hydroxyl as a substituent, hydroxyl group, or protected hydroxyl group; and $R^3$ is a hydrogen atom or carboxylic acid protective group $R^4$—CHO (2)

wherein $R^4$ is a hydrogen atom, or lower alkyl group which may have a substituent (3)

wherein $R^1$, $R^2$, $R^3$ and $R^4$ are as defined above.

With the conventional processes for preparing 3-alkenylcephem compounds by employing Wittig reaction, not only any satisfactory yield is obtained, but also it is time-consuming to purify the desired compound due to the by-product generated in the reactions. The inventor found that the reason for these was to allow unstable intermediates to reside for a long time during the isolation or in the system, and succeeded in preparing 3-vinylcephem compounds at high yield and purity when a reaction system for minimizing the residence time of such intermediates was discovered. Under the reaction conditions of the invention, the unstable intermediates react quickly with the reagents in the system, resulting in a 3-alkenylcephem compound. Therefore, examples of cephem compounds, the existence of which is recognizable in the system, are stable 3-chloromethylcephem compounds and 3-alkenylcephem compounds.

The wavy line bonded to $R^4$ of the formula (3) of the invention denotes a stereoisomer and means that against the double bond of 3-alkenyl group, $R^4$ is cis alone, trans alone, or a cis/trans mixture.

Examples of the groups described in the present specification are as follows:

Halogen atom means fluorine, chlorine, bromine, iodine, or the like.

Lower alkyl group means, for example, a straight-chain or branched $C_1$~$C_4$ alkyl groups such as methyl, ethyl, n-propyl, isopropyl, n-butyl, isobutyl, sec-butyl and tert-butyl. Aryl group means, for example, phenyl, anisyl or naphthyl.

Examples of the protected amino group represented by $R^1$ are formamido, phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, phenylacetoxyacetamido, α-oxophenylacetamido, thienylacetamido, benzamido, p-methylbenzamido, p-t-butylbenzamido, p-methoxybenzamido, p-chlorobenzamido, p-bromobenzamido, etc. In addition to these, there are the groups disclosed in "Protective Groups in Organic Synthesis written by Theodora W. Greene, 1981, by John Wiley & Sons. Inc." (hereinafter referred to merely as the "literature"), Chap. 7 (pp. 218–287), and phenylglycylamido, phenylglycylamido in which amino group is protected, p-hydroxyphenylglycylamido, and p-hydroxyphenylglycylamido in which either of amino and hydroxyl, or both of these are protected. Examples of protective groups for the amino of phenylglycylamido group and p-hydroxyphenylglycylamido group are those disclosed in the literature, Chap. 7 (pp. 218–287). Examples of protective groups for the hydroxyl of p-hydroxyphenylglycylamido are those disclosed in the literature, Chap. 2 (pp. 10–72).

Examples of the aryl of Ar—CH=N— group are phenyl and phenyl groups which may have a substituent, such as p-methoxyphenyl, p-nitrophenyl and m-hydroxyphenyl.

Exemplary of the substituent which may be substituted in the aryl represented by Ar are halogen atom; hydroxyl; nitro; cyano; aryl; lower alkyl; amino; mono-lower alkylamino; di-lower alkylamino; mercapto; alkylthio or arylthio represented by group $R^7S$— ($R^7$ is a lower alkyl or aryl); formyloxy; acyloxy represented by group $R^6COO$— ($R^6$ is hydrogen atom, lower alkyl, or aryl); formyl; acyl represented by group $R^6CO$— ($R^6$ is as defined above); alkoxy or aryloxy represented by group $R^6O$— ($R^6$ is as defined above); carboxyl; and alkoxylcarbonyl or aryloxycarbonyl represented by group $R^6OCO$— ($R^6$ is as defined above). The aryl represented by Ar is substituted by substituents of the same or different kinds selected from among the above substituents, and at least one substituent may be substituted in the same or different carbon.

Examples of the lower alkoxy represented by $R^2$ are straight-chain or branched $C_1$~$C_4$ alkoxy groups such as methoxy, ethoxy, n-propoxy, isopropoxy, n-butoxy, isobutoxy, sec-butoxy and tert-butoxy.

Examples of the lower acyl represented by $R^2$ are straight-chain or branched $C_1$~$C_4$ acyl groups such as formyl, acetyl, propionyl, butyryl and isobutyryl.

Examples of protected hydroxyl groups for lower alkyl represented by $R^2$ and substituted with hydroxyl group or protected hydroxyl group, and examples of protective groups for the protected hydroxyl represented by $R^2$, are those disclosed in the literature, Chap. 2 (pp. 10–72). The above lower alkyl groups represented by $R^2$ is substituted by substituents of the same or different kinds selected from among hydroxyl group and the protected hydroxyl groups as defined above, and at least one of such substituents may be substituted in the same or different carbon.

Exemplary of the carboxylic acid protecting groups represented by $R^3$ are benzyl, p-methoxybenzyl, p-nitrobenzyl, diphenylmethyl, trichloroethyl, tert-butyl, or the groups described in the literature, Chap. 5 (pp. 152–192).

Exemplary of the lower alkyl groups which may have a substituent represented by $R^4$ are straight-chain lower alkyl groups such as methyl, ethyl and propyl; branched lower alkyl groups such as isopropyl and isobutyl; and halogenated lower alkyl groups such as chloromethyl and bromomethyl. Besides these, it is possible to use the lower alkyl groups having a substituent which may be substituted in the aryl represented by the above Ar.

In the present invention, 3-chloromethylcephem compounds of the formula (1), which are used as a starting material, are prepared by, for example, the method described in literature [(Torii et al., Tetrahedron Lett., 23, pp. 2187–2188 (1982)].

In accordance with the present invention, a 3-chloromethylcephem compound of the formula (1) to be prepared by the above method is reacted with, for example, triphenylphosphine and formaldehyde in the presence of iodization reagent and alkali metal hydroxide or carbonate, thereby obtaining a 3-vinylcephem compound of the formula (2).

Examples of iodization reagents are alkali metal iodide salts such as lithium iodide, sodium iodide and potassium iodide; alkaline earth metal iodide salts such as calcium iodide; ammonium iodide; and quaternary ammonium iodide salts such as tetraethyl ammonium iodide. These iodization reagents can be used singly or in a combination of at least two of them. These iodization reagents are usually used in an amount of one to three moles, preferably one to two moles, per mole of the compound of the formula (1). These iodization reagents can be used in the form of an aqueous solution.

Examples of alkali metal hydroxide or carbonate are lithium hydroxide, sodium hydroxide, potassium hydroxide, lithium carbonate, sodium carbonate and potassium carbonate. These alkali metal hydroxides or carbonates can be used singly or in a mixture of at least two of them. These alkali metal hydroxides or carbonates are usually used in an amount of one to ten moles, preferably one to three moles, per mole of the compound of the formula (1). These alkali metal hydroxides or carbonates can be used in the form of an aqueous solution.

As the arylphosphine used in the present invention, there are triphenylphosphine which may have a substituent, such as triphenylphosphine and tri-p-methoxyphenylphosphine. As the groups that can be substituted for phenyl, it is possible to use the substituents which may be substituted for the aryl represented by the above Ar. Triarylphosphine is usually used in an amount of one to five moles, preferably one to three moles, per mole of the compound of the formula (1).

Examples of aldehydes of the formula (2) used in the present invention are straight-chain or branched lower alkylaldehydes which may have a substituent, such as formaldehyde, acetaldehyde, chloroacetaldehyde and isobutylaldehyde; and arylaldehydes which may have a substituent, such as benzaldehyde, tolylaldehyde and anisaldehyde. As the substituent that may be substituted for lower alkyl and aryl, it is possible to use all the substituents that may be substituted for the aryl represented by the above Ar. The aldehyde of the formula (2) is usually used in an amount of 1 to 30 moles, preferably 1 to 15 moles, per mole of the ccmpound of the formula (1). It is not particularly required to use the aldehyde of the formula (2) in gaseous form, or use the aldehyde anhydride. The aldehyde in the form of an aqueous solution is also usable.

Examples of solvents are ketones such as acetone; ethers such as tetrahydrofuran (THF) and dioxane; hydrocarbon halides such as methylene chloride and chloroform; nitriles such as acetonitrile, propionitrile, butyronitrile, isobutyronitrile and valeronitrile; and dimethyl sulfoxide. These can be used singly or in a mixture of at least two of them. Alternatively, it is possible to use a mixed solvent in which the above solvent is used mainly and other usual solvents are added thereto. As the usual solvents, there are, for example, lower alkyl esters of lower carboxylic acids such as methyl formate, ethyl formate, propyl formate, butyl formate, methyl acetate, ethyl acetate, propyl acetate, butyl acetate, methyl propionate and ethyl propionate; ethers such as diethyl ether, ethyl propyl ether, ethyl butyl ether, dipropyl ether, diisopropyl ether, dibutyl ether, methylcellosolve and dimethoxyethane; cyclic ethers such as tetrahydrofuran and dioxane; substituted or unsubstituted aromatic hydrocarbons such as benzene, toluene, xylene, chlorobenzene and anisole; hydrocarbons such as pentane, hexane, heptane and octane; cycloalkanes such as cyclopentane, cyclohexane, cycloheptane and cyclooctane; and halogenated hydrocarbons such as dichloromethane, chloroform, dichloroethane, trichloroethane, dibromoethane, propylene dichloride and carbon tetrachloride. Particularly preferred solvent are mixed solvents of which main solvent is dimethylformamide, 1-methyl-2-pyrrolidinone or dimethyl sulfoxide. The above solvents are not required to be anhydrous, and hydrous solvents are also usable.

These solvents are used in an amount of about 0.5 to 200 liter, preferably about 1 to 50 liter, per 1 kg of the compound of the formula (1).

The reaction is conducted in the range of −10 to 80° C., preferably 0 to 50° C.

The compound of the formula (2) can be obtained as an approximately pure product, by performing, after the reaction is terminated, the usual extraction or crystallization. It is, of course, possible to purify by any other method.

Suitable solvents are mixed solvents corprising mainly dimethylformamide, 1-methyl-2-pyrrolidinone or dimethyl sulfoxide. These solvents are not required to be anhydrous, and hydrous solvents are also usable.

BEST MODE OF CARRYING OUT THE INVENTION

The present invention will be described in further detail by the following examples.

EXAMPLE 1

After weighing out 100 mg of a compound of the formula (1) ($R^1$=phenylacetamido, $R^2$=H, $R^3$=p-methoxybenzyl, "compound 1a"), 42 mg of potassium iodide and 82 mg of triphenylphosphine, 2 ml of methylene chloride and 1 ml of acetone were added thereto. To this, 0.46 ml of 10% aqueous solution of sodium carbonate and 0.17 ml of 36% aqueous solution of formaldehyde were added and stirred at a temperature of 22° C. to 25° C., for 18 hours. This reaction solution was diluted with methylene chloride, and then washed with water three times. The obtained methylene chloride solution was concentrated under reduced pressure, and purified by silica gel column chromatography, to give 86 mg of a desired 3-vinylcephem compound ($R^1$=phenylacetamido, $R^2$=H, $R^3$=p-methoxybenzyl, $R^4$=H, "compound 2a") (yield: 90%).

$^1$H NMR (300 MHz, CDCl$_3$) δ 3.44(d, J=18 Hz, 1H), 3.60(d, J=16 Hz, 1H), 3.61(d, J=18 Hz, 1H), 3.67(d, J=16 Hz, 1H), 3.79(s, 3H), 4.92(d, J=4.4 Hz, 1H), 5.16(d, J=14 Hz, 1H), 5.21(d, J=14 Hz, 1H), 5.31(d, J=11 Hz, 1H), 5.43(d, J=17 Hz, 1H), 5.81(dd, J=4.4, 9 Hz, 1H), 6.26(d, J=9 Hz, 1H), 7.08(dd, J=44, 17 Hz, 1H), 6.85–7.40(m, 9H).

EXAMPLE 2

The reaction was conducted in the same manner as in Example 1 except that 0.52 ml of 10% aqueous solution of sodium carbonate was used as the base, to obtain 84 mg of the desired 3-vinylcephem compound 2a (yield: 88%).

EXAMPLE 3

The reaction was conducted in the same manner as in Example 1 except that 38 mg of sodium iodide was used in place of potassium iodide, to obtain 86 mg of the desired 3-vinylcephem compound 2a (yield: 90%).

EXAMPLES 4 to 8

The reaction was conducted in the same manner as in Example 1 except that the solvent was changed as follows. Table 1 gives the results.

TABLE 1

| Example | solvent-1 (ml) | solvent-2 (ml) | yield (%) |
|---|---|---|---|
| 4 | methylene chloride (2) | THF (1) | 88 |
| 5 | methylene chloride (2) | dioxane (1) | 85 |
| 6 | ethyl acetate (2) | acetone (1) | 89 |

TABLE 1-continued

| Example | solvent-1 (ml) | solvent-2 (ml) | yield (%) |
|---|---|---|---|
| 7 | methylene chloride (1) | acetone (1) | 85 |
| 8 | methylene chloride (1) | THF (1) | 80 |

EXAMPLE 9

After weighing out 100 mg of a compound of the formula (1) ($R^1$=phenylacetamido, $R^2$=H, $R^3$=diphenylmethyl, "compound 1b"), 38 mg of potassium iodide and 75 mg of triphenylphosphine, 2 ml of methylene chloride and 1 ml of acetone were added thereto. To this, 0.42 ml of 10% aqueous solution of sodium carbonate and 0.16 ml of 36% aqueous solution of formaldehyde were added and stirred at a temperature of 22° C. to 25° C., for 19 hours. This reaction solution was diluted with methylene chloride, and then washed with water three times. The obtained methylene chloride solution was concentrated under reduced pressure, and purified by silica gel column chromatography, to give 90 mg of a desired 3-vinylcephem compound ($R^1$=phenylacetamido, $R^2$=H, $R^3$=diphenylmethyl, $R^4$=H, "compound 2b") (yield: 94%).

$^1$H-NMR(300 MHz, DMSO-d$_6$) δ 3.49(d, J=14 Hz, 1H), 3.57(d, J=14 Hz, 1H), 3.58(d, J=18 Hz, 1H), 3.91(d, J=18 Hz, 1H), 5.18(d, J=5.1 Hz, 1H), 5.28(d, J=11 Hz, 1H), 5.63(d, J=17 Hz, 1H), 5.75(dd, J=5.1, 8.1 Hz, 1H), 6.70(dd, J=11, 17 Hz, 1H), 6.939(s, 1H), 9.17(d, J=8.1 Hz, 1H), 7.19–7.46(m, 15H).

EXAMPLE 10

After weighing out 100 mg of a compound of the formula (1) ($R^1$=p-CH$_3$OC$_6$H$_4$CH=N—, $R^2$=H, $R^3$=p-methoxybenzyl, "compound 1c"), 41 mg of potassium iodide and 113 mg of triphenylphosphine, 2 ml of methylene chloride and 1 ml of acetone were added thereto. To this, 0.46 ml of 10% aqueous solution of sodium carbonate and 0.17 ml of 36% aqueous solution of formaldehyde were added and stirred at a temperature of 22° C. to 25° C., for 20 hours. This reaction solution was diluted with methylene chloride, and then washed with water three times. The obtained methylene chloride solution was concentrated under reduced pressure, and crystallized with methanol, to give 82 mg of a desired 3-vinylcephem compound ($R^1$=p-CH$_3$OC$_6$H$_4$CH=N—, $R^2$=H, $R^3$=p-methoxybenzyl, $R^4$=H, "compound 2c") (yield: 86%).

$^1$H-NMR(300 MHz, CDCl$_3$) δ 3.48(d, J=17 Hz, 1H), 3.67(d, J=17 Hz, 1H), 3.80(s, 3H), 3.84(s, 3H), 5.14(d, J=5.0 Hz, 1H), 5.20(d, J=11 Hz, 1H), 5.27(d, J=11 Hz, 1H), 5.29(d, J=12 Hz, 1H), 5.36(dd, J=1.8, 5.0 Hz, 1H), 5.45(d, J=17 Hz, 1H), 6.88(d, J=9 Hz, 2H), 6.93(d, J=9 Hz, 2H), 7.05(dd, J=11, 17 Hz, 1H), 7.36(J=9 Hz, 2H), 7.71(J=9 Hz, 1H), 8.54(d, J=1.8 Hz, 1H).

EXAMPLE 11

After weighing out 100 mg of a compound of the formula (1) ($R^1$=phenylacetamido, $R^2$=H, $R^3$=p-methoxybenzyl, "compound 1d"), 41 mg of potassium iodide and 113 mg of triphenylphosphine, 2 ml of methylene chloride and 1 ml of acetone were added thereto. To this, 0.46 ml of 10% aqueous solution of sodium carbonate and 0.20 ml of 40% aqueous solution of chloroacetaldehyde were added and stirred at a temperature of 22° C. to 25° C., for 22 hours. This reaction solution was diluted with methylene chloride, and then washed with water three times. The obtained methylene chloride solution was concentrated under reduced pressure, and purified by silica gel column chromatography, to give 90 mg of a desired 3-chloropropenylcephem compound ($R^1$=phenylacetamido, $R^2$=H, $R^3$=p-methoxybenzyl, $R^4$=chloromethyl, "compound 2d") (yield: 85%).

$^1$H-NMR(300 MHz, DMSO-d6) d 3.55(s, 2H), 3.76(s, 3H), 3.93(dd, J=8, 12 Hz, 1H), 4.16(dd, J=8, 12 Hz, 1H), 5.14(ABq, J=12 Hz, 2H), 5.21(d, J=5.0 Hz, 1H), 5.70(dt, J=8, 11 Hz, 1H), 5.74(dd, J=5.0, 8.0 Hz, 1H), 6.30(d, J=11 Hz, 1H), 6.90–7.40(m, 9H), 9.14(d, J=8.0, Hz, 1H).

EXAMPLE 12

After weighing out 100 mg of a compound of the formula (1) ($R^1$=formamido, $R^2$=H, $R^3$=p-methoxybenzyl, "compound 1e"), 33 mg of potassium iodide and 92 mg of triphenylphosphine, 2 ml of methylene chloride and 1 ml of acetone were added thereto. To this, 0.37 ml of 10% aqueous solution of sodium carbonate and 0.16 ml of 40% aqueous solution of chloroacetaldehyde were added and stirred at a temperature of 22° C. to 25° C., for 18 hours. This reaction solution was diluted with methylene chloride, and then washed with water three times. The obtained methylene chloride solution was concentrated under reduced pressure, and purified by silica gel column chromatography, to give 93 mg of a desired 3-chloropropenylcephem compound ($R^1$=formamido, $R^2$=H, $R^3$=p-methoxybenzyl, $R^4$=chloromethyl, "compound 2e") (yield: 87%).

$^1$H-NMR(300 MHz, DMSO-$d_6$) δ 3.29(d, J=18 Hz, 1H), 3.54(d, J=18 Hz, 1H), 3.71(dd, J=8, 12 Hz, 1H), 3.78(s, 3H), 3.96(d, J=8, 12 Hz, 1H), 5.00(d, J=5.0 Hz, 1H), 5.13(s, 2H), 5.71(dt, J=12, 8 Hz, 1H), 5.86(dd, J=5.0, 8.0 Hz, 1H), 6.23(d, J=12 Hz, 1H), 6.44(d, J=8.0 Hz, 1H), 6.83(d, J=9 Hz, 2H), 7.27(d, J=9 Hz, 2H), 8.22(s, 1H).

REFERENCE EXAMPLE 1

The 3-vinylcephem compounds 2a and 2b obtained in Examples 1 and 9, respectively, can be converted to Cefixime according to the following procedure.

After the compound 2a or 2b was reacted with phosphorus pentachloride/pyridine reagent by using methylene chloride as a solvent, the reaction solution was cooled to –35° C. and treated with methanol, to form 7-amino-3-vinylcephem hydrochloride. To this, phenol was added and reacted at 45° C. for one hour, to give 7-amino-3-vinylcephem-4-carboxylic acid. This can be converted to Cefixime by the method described in JP-B-20435/1988.

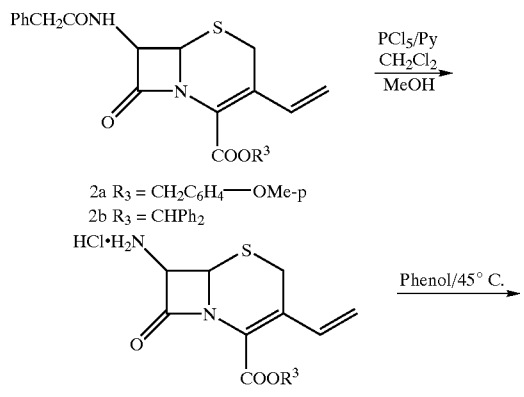

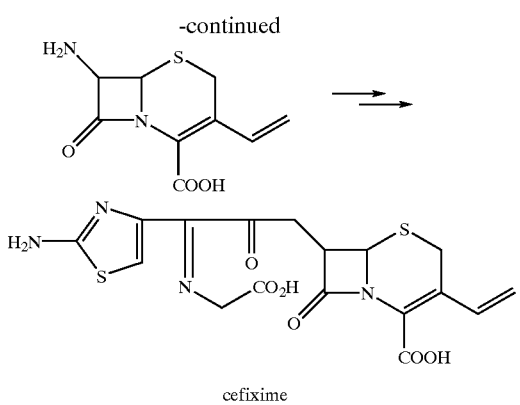

cefixime

REFERENCE EXAMPLE 2

The 3-vinylcephem compound 2c obtained in Example 10 can be converted to Cefixime according to the following procedure.

When the compound 2c was reacted with m-cresol and concentrated hydrochloric acid, the reaction proceeded in a single step, to give 7-amino-3-vinylcephem-4-carboxylic acid. This can be converted to Cefixime by the method described in JP-B-20435/1988, as in Reference Example 1.

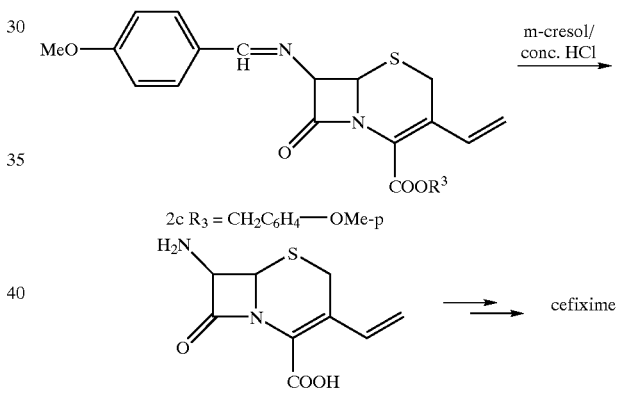

INDUSTRIAL APPLICABILITY

The present invention provides a process for preparing 3-alkenylcephem compounds that are the intermediates of useful antibacterial agents having a wide range antibacterial spectrum.

In accordance with the invention, since the reaction reagent is allowed to reside simultaneously in the system, unstable intermediates reside for a short period of time. This permits a high yield of the desired 3-alkenylcephem compounds and also produces less by-product due to the decomposition reaction of the intermediates. There is also the feature that the reaction is facilitated enormously by the coexistence of the reaction reagent in the system. In addition, neither expensive palladium compounds nor copper catalysts are required, and there is no need to use unstable allene compounds, and 3-trifluoromethanesulfonyloxycephem compounds or fluoromethanesulfonyloxycephem compound, the industrial production of which is difficult. Therefore, the process of the invention is extremely excellent industrially.

What is claimed is:

1. A process for preparing a 3-alkenylcephem compound of formula (3)

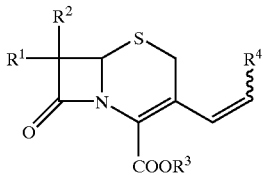

(3)

wherein
- $R^1$ is a hydrogen atom, a halogen atom, an amino group, a protected amino group, or an Ar—CH=N— group, wherein Ar is an aryl group, a naphthyl group, or a phenyl group which is unsubstituted or substituted, by at least one of a halogen atom, a hydroxyl, a nitro, a cyano, an aryl, a lower alkyl, an amino, a mono-lower alkylamino, a di-lower alkylamino, a mercapto, a formyloxy, a formyl, a carboxyl, an alkylthio or an arylthio represented by formula $R^7S$—,
- wherein $R^7$ of formula $R^7S$— is a lower alkyl or aryl, or an acyloxy represented by formula $R^6COO$—,
- wherein $R^6$ of formula $R^6COO$— is a lower alkyl, an aryl, or an acyl represented by formula $R^6CO$—,
- wherein $R^6$ of formula $R^6CO$— is a lower alkyl, an aryl, an alkoxy, or an aryloxy represented by formula $R^6O$—,
- wherein $R^6$ of formula $R^6O$— is a lower alkyl or an aryl, or an alkoxycarbonyl or an aryloxycarbonyl represented by formula $R^6OCO$—,
- wherein $R^6$ of formula $R^6OCO$— is a lower alkyl or an aryl, and further wherein the substituent group is the same or different, and at least one substituent on the substituted phenyl group is substituted on the same or a different carbon atom,
- $R^2$ is a hydrogen atom, a halogen atom, a lower alkoxy group, a lower acyl group wherein the lower acyl group is a straight or branched $C_1$–$C_4$ acyl group, a lower alkyl group, a lower alkyl group which has a hydroxyl or protected hydroxyl as a substituent, a hydroxyl group or a protected hydroxyl group,
- $R^3$ is a hydrogen atom or a carboxylic acid protective group, and
- $R^4$ is a hydrogen atom or a lower alkyl group selected from the group consisting of a straight-chain lower alkyl group such as methyl, ethyl and propyl, a branched lower alkyl group, and a halogenated lower alkyl, said process comprising adding the following compounds in the order of a) a 3-chloromethylcepham compound of formula (1)

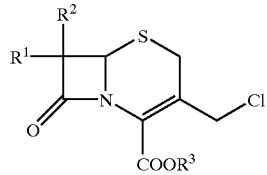

(1)

wherein $R^1$, $R^2$ and $R^3$ are as defined above, b) an iodization reagent wherein the iodization reagent is an alkali metal iodide of potassium iodide, an alkaline earth metal iodide salt, ammonium iodide or a quarternary ammonium iodide salt, c) an arylphosphine where aryl is a naphthyl group or an unsubstituted or substituted phenyl group, wherein a substituent group for the substituted phenyl group is the same or different, and thereafter d) an alkali metal hydroxide or carbonate, and e) an aldehyde of formula (2)

$$R^4\text{—CHO} \qquad (2),$$

wherein $R^4$ is defined as above, and
reacting the compounds of a)–e) in a single step reaction for forming the 3-alkenyl cephem compound.

2. The process of claim 1, wherein the aldehyde of formula (2) is formaldehyde, acetaldehyde or chloroacetaldehyde.

3. The process of claim 1, wherein the iodization reagent is sodium iodide or potassium iodide.

4. The process of claim 1, wherein the arylphosphine is triphenylphosphine.

* * * * *

UNITED STATES PATENT AND TRADEMARK OFFICE
CERTIFICATE OF CORRECTION

PATENT NO. : 6,417,351 B1
DATED : July 9, 2002
INVENTOR(S) : Kaymeyama

It is certified that error appears in the above-identified patent and that said Letters Patent is hereby corrected as shown below:

<u>Title page,</u>
Item [22], please change the PCT Filed date from "Apr. 6, 1998" to -- June 4, 1998 --.

Signed and Sealed this

Thirty-first Day of December, 2002

JAMES E. ROGAN
*Director of the United States Patent and Trademark Office*